United States Patent
Lewis (12)

(10) Patent No.: US 10,052,473 B2
(45) Date of Patent: Aug. 21, 2018

(54) GENDERLESS CONNECTOR AND METHOD OF FLUID CONNECTION

(71) Applicant: Nordson Corporation, Westlake, OH (US)

(72) Inventor: Peter D. Lewis, Fort Collins, CO (US)

(73) Assignee: Nordson Corporation, Westlake, OH (US)

( * ) Notice: Subject to any disclaimer, the term of this patent is extended or adjusted under 35 U.S.C. 154(b) by 217 days.

(21) Appl. No.: 14/685,901

(22) Filed: Apr. 14, 2015

(65) Prior Publication Data

US 2015/0306366 A1 Oct. 29, 2015

Related U.S. Application Data

(60) Provisional application No. 61/983,704, filed on Apr. 24, 2014.

(51) Int. Cl.
*A61M 39/10* (2006.01)
*F16L 37/248* (2006.01)

(52) U.S. Cl.
CPC ........ *A61M 39/1011* (2013.01); *A61M 39/10* (2013.01); *F16L 37/248* (2013.01); *A61M 2039/1033* (2013.01); *A61M 2039/1094* (2013.01); *A61M 2207/00* (2013.01)

(58) Field of Classification Search
CPC .. A61M 2039/1033; A61M 2039/1094; A61M 2207/00; A61M 39/10; A61M 39/1011; F16L 37/248
See application file for complete search history.

(56) References Cited

U.S. PATENT DOCUMENTS

| | | |
|---|---|---|
| 508,448 A | 11/1893 | Terlinden |
| 770,049 A | 9/1904 | Dorgans |
| 939,436 A | 11/1909 | McVoy |

(Continued)

FOREIGN PATENT DOCUMENTS

| | | |
|---|---|---|
| CN | 1124337 A | 6/1996 |
| CN | 1200796 A | 12/1998 |

(Continued)

OTHER PUBLICATIONS

CN Office Action dated Mar. 5, 2018 for CN Application No. 201510290449.

*Primary Examiner* — Bhisma Mehta
*Assistant Examiner* — Brandy S Lee
(74) *Attorney, Agent, or Firm* — Baker & Hostetler LLP (57) ABSTRACT

A fluid connector includes first and second fluid connector elements with respective first and second base portions. The first and second fluid connector elements each include a pair of extension portions extending from the respective first and second base portions. First and second face seal elements are respectively carried by the first and second base portions and are contained within the pair of extension portions of the associated fluid connector element. A locking coupling allows the first and second fluid connector elements to be coupled together with the face seal elements in facing and sealing engagement, and then rotated relative to one another and locked together to form a fluid tight joint between the face seal elements and a fluid flow path through the first and second face seal elements and the first and second fluid connector elements.

12 Claims, 6 Drawing Sheets

(56) References Cited

U.S. PATENT DOCUMENTS

| | | | |
|---|---|---|---|
| 974,517 | A | 11/1910 | Revaillot |
| 1,303,367 | A | 5/1919 | Nelson |
| 2,204,392 | A | 6/1940 | Arm |
| 2,690,542 | A | 9/1954 | Pearce et al. |
| 2,950,130 | A | 8/1960 | Schneider |
| 3,104,896 | A | 9/1963 | Kennedy, Jr. |
| 3,195,931 | A | 7/1965 | Braunagel |
| 3,700,269 | A | 10/1972 | Salata |
| 4,418,946 | A | 12/1983 | Gambon |
| 5,118,303 | A | 6/1992 | LeBaron et al. |
| 5,645,302 | A | 7/1997 | Horimoto |
| 5,779,277 | A | 7/1998 | Street |
| 6,325,425 | B1 | 12/2001 | Kierath et al. |
| 7,137,654 | B2 | 11/2006 | Segal et al. |
| 8,376,412 | B2 * | 2/2013 | Johnson .............. F16L 37/0985 285/336 |
| 2010/0230961 | A1 * | 9/2010 | Johnson .............. F16L 37/0985 285/352 |
| 2011/0046566 | A1 | 2/2011 | Elahi et al. |

FOREIGN PATENT DOCUMENTS

| | | |
|---|---|---|
| CN | 1250513 A | 4/2000 |
| CN | 1311704 A | 9/2001 |
| CN | 101541364 A | 9/2009 |
| FR | 0008970 E | 8/1908 |
| FR | 2328915 A1 | 5/1977 |
| GB | 0883008 | 11/1961 |
| WO | 2012160123 A1 | 11/2012 |

* cited by examiner

GENDERLESS CONNECTOR AND METHOD OF FLUID CONNECTION

CROSS-REFERENCE TO RELATED APPLICATION

This application claims the benefit of U.S. Provisional Patent Application No. 61/983,704, filed on Apr. 24, 2014, the disclosure of which is incorporated by reference herein in its entirety.

TECHNICAL FIELD

The present invention generally relates to fluid connectors and, more particularly, to genderless fluid connectors.

BACKGROUND

Many traditional fluid connectors have a male component and a female component that couple together for making a fluid connection, such as between two lengths of flexible tubing, or in other fluid applications. This presents various challenges such as the need to manufacture and stock different components. Certain genderless fluid connectors are known and do not require a male and female component, however, these can present other challenges or problems such as the inability to reuse the connector.

SUMMARY

In an illustrative embodiment of the invention, a fluid connector is provided and comprises first and second fluid connector elements including respective first and second base portions. The first and second fluid connector elements each includes a pair of extension portions extending from the respective first and second base portions. The fluid connector also includes first and second face seal elements respectively carried by the first and second base portions and contained within the pair of extension portions. A locking coupling is configured to allow the first and second fluid connector elements to be coupled together with the face seal elements in facing and sealing engagement. The first and second fluid connector elements are then rotated relative to one another and locked together to form a fluid tight joint between the face seal elements, and to form a fluid flow path through the first and second face seal elements and the first and second fluid connector elements. The locking coupling may take any suitable form for locking the two fluid connector elements in fluid tight engagement. In the illustrative embodiment the locking coupling is a bayonet type coupling. In another aspect, one or both of the face seal elements rotate(s) with respect to its associated fluid connector element as the first and second fluid connector elements are rotated relative to one another and locked together.

In another embodiment, a fluid system is provided and comprises a fluid connector such as described above, coupled with first and second tubes. The first and second tubes are respectively coupled to the first and second face seal elements. For example, the face seal elements may each have a barbed protrusion that receives the end of a piece of flexible tubing. When the first and second fluid connector elements are rotated relative to one another and locked together, a fluid tight joint is formed between the face seal elements and a fluid flow path is formed through the first and second face seal elements, the first and second fluid connector elements and the first and second tubes.

In another aspect, the invention provides a method of forming a fluid tight connection which includes mating first and second fluid connector elements such that respective first and second face seal elements carried within the first and second fluid connector elements are in opposed relation. At least one of the first or second fluid connector elements is rotated with respect to the other to force the first and second face seal elements into facing, sealing engagement. The face seal elements are then locked in the facing, sealing engagement with each other to form a fluid tight joint between the face seal elements and to form a fluid flow path through the first and second face seal elements and the first and second fluid connector elements.

Various additional features and advantages will become readily apparent to those of ordinary skill in the art upon review of the following detailed description of the illustrative embodiments, taken in conjunction with the accompanying drawings.

DETAILED DESCRIPTION

Figure 1:
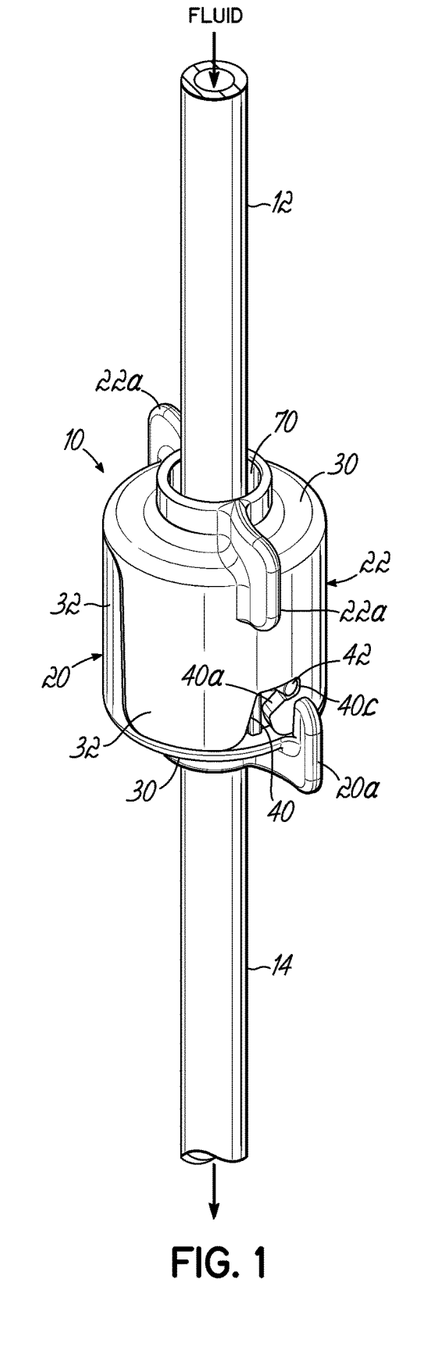
FIG. 1 is a perspective view of a fluid system including a pair of flexible tubes coupled together by a fluid connector constructed in accordance with an illustrative embodiment of the invention.
Figure 2A:
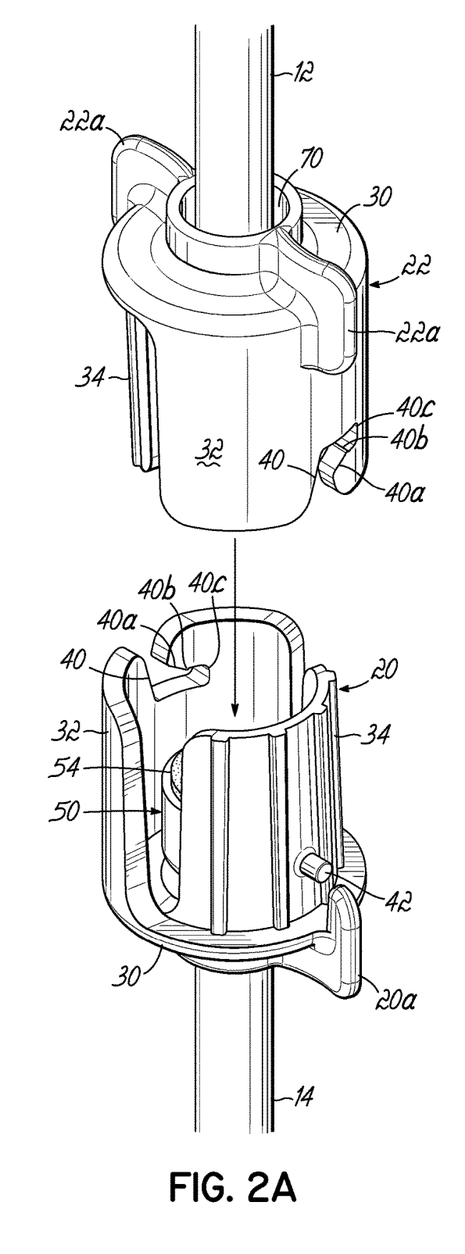
FIG. 2A is a disassembled perspective view of the system shown in FIG. 1.
Figure 2B:
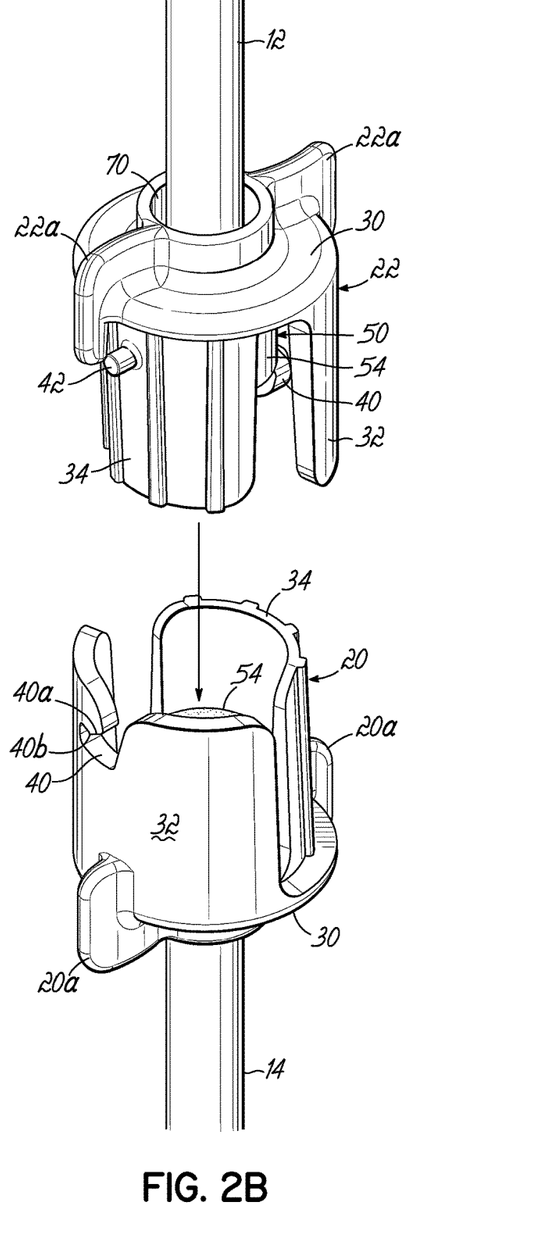
FIG. 2B is a disassembled perspective view of the system shown in FIG. 2A but rotated approximately 90°.
Figure 3:
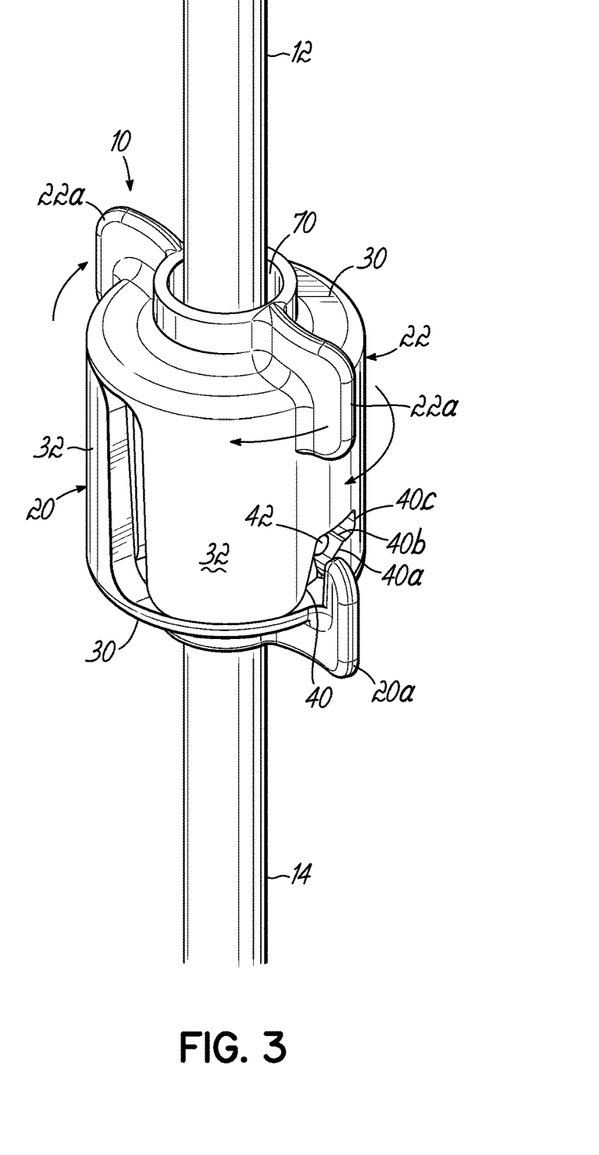
FIG. 3 is a perspective view similar to FIG. 1, but showing the connector before it is rotated to a fully coupled position.
Figure 4:
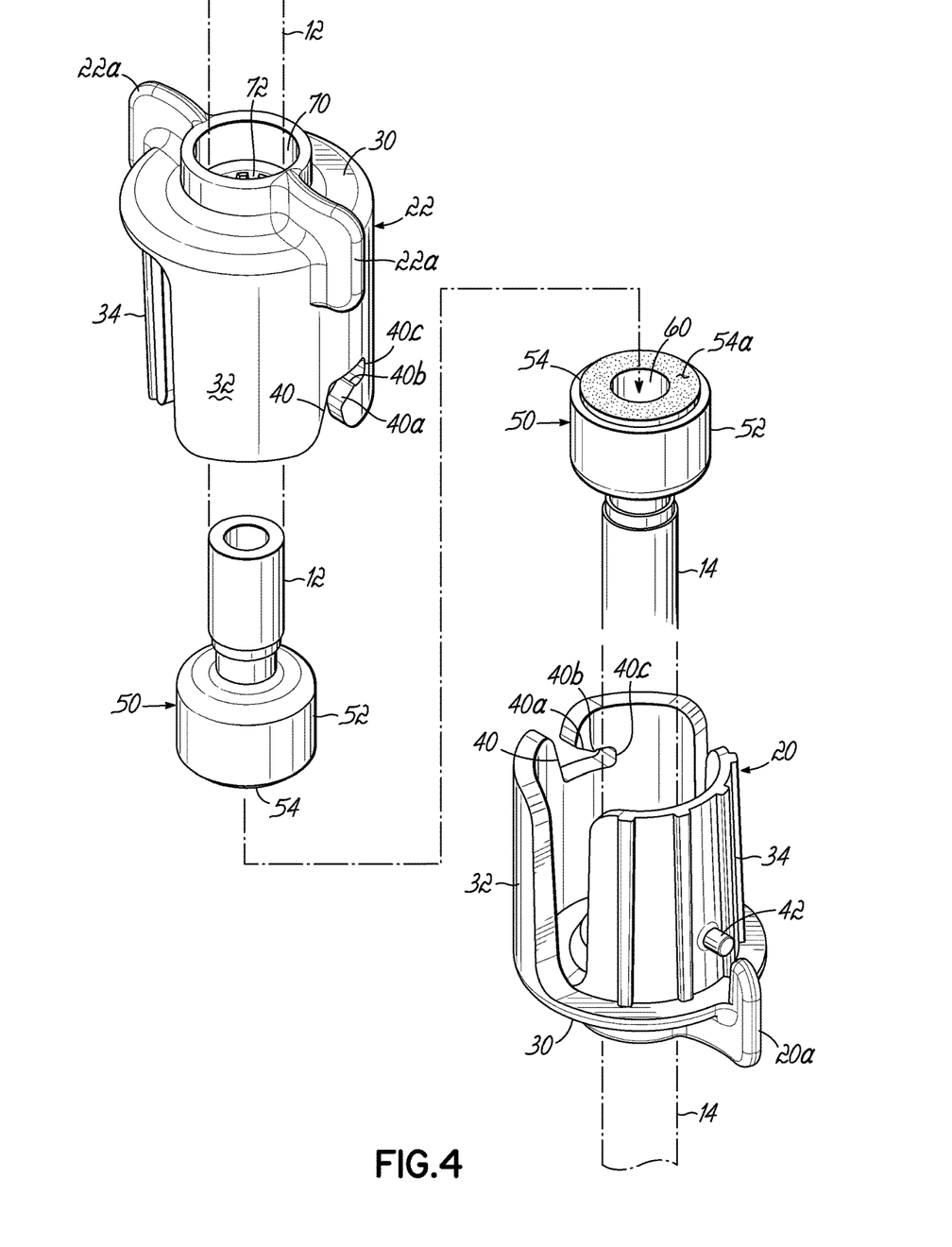
FIG. 4 is a disassembled perspective view illustrating component parts of each connector element.
Figure 5A:
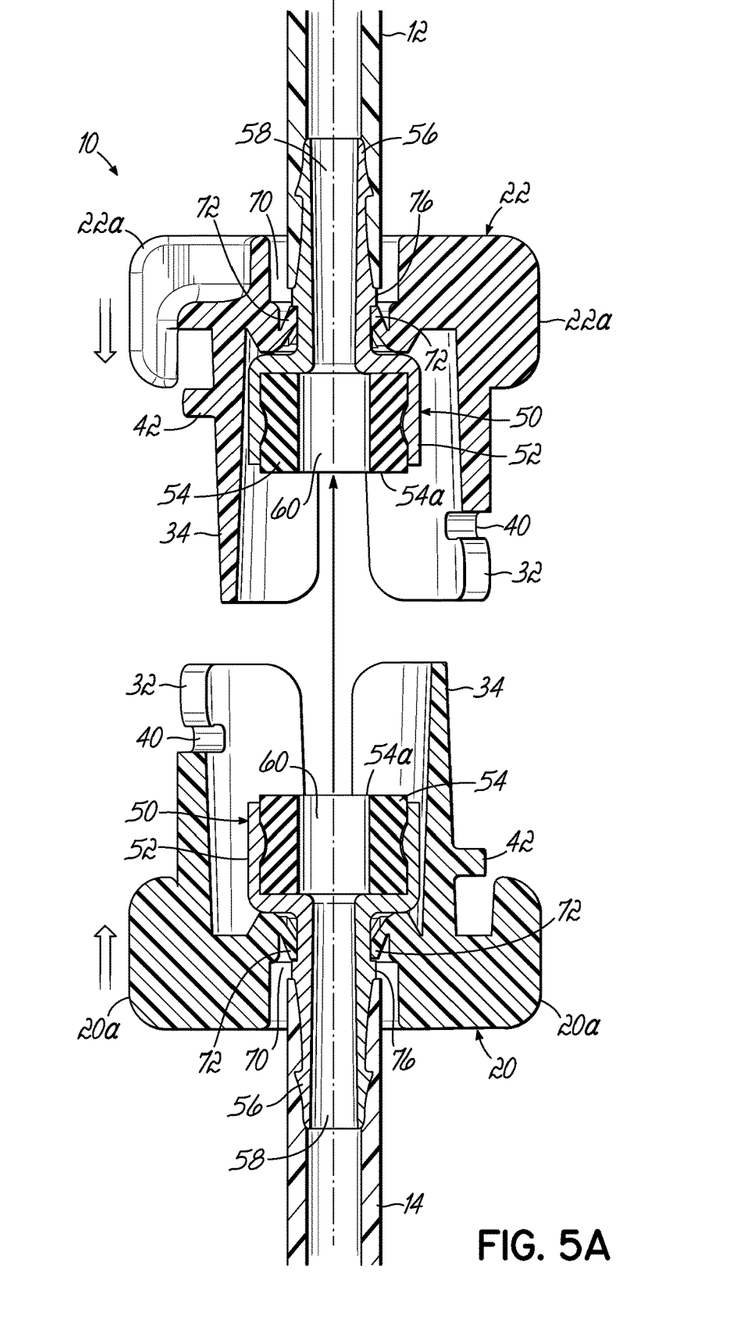
FIG. 5A is a longitudinal axial cross sectional view of the system with the connector elements uncoupled from each other.

FIGS. 1, 2A, 2B and 3 show an illustrative embodiment of a genderless connector 10 that may be reused. The connector 10 may be used, for example, in the healthcare industry to connect two lengths of flexible medical tubing 12, 14 together. The medical tubing 12, 14 may be of various types but standard silicone tubing is shown and described herein. The connector 10 and tubing 12, 14 are considered a fluid system herein, but it will be understood that the fluid system may be comprised of different and/or further fluid components depending on the application needs. The connector 10 is comprised of two connector elements 20, 22, each identical to the other. The two connector elements 20, 22 are coupled together with a partial rotation as understood from comparing FIG. 1, which illustrates the rotated and locked condition, to FIG. 3 which illustrates an initial condition in which the two connector elements 20, 22 have been mated together but not rotated with respect to one another into the locked condition. The connection is generally similar to a bayonet connection and, in this embodiment, the partial rotation involves a turn of approximately 26° to lock the two connector elements 20, 22 together. The bayonet type connection may be replaced with any suitable locking coupling. As will be appreciated from the description to follow, as well as the drawings, the connector elements 20, 22 may be repeatedly de-coupled and re-coupled. In this manner, the connector 10 may be easily re-used. The connector elements 20, 22 include finger tabs 20a, 22a to assist with rotating at least one of the connector elements 20, 22 with respect to the other as generally shown in FIG. 3. As further shown in FIGS. 2A and 2B, each connector element 20, 22 comprises a base portion 30 and two curved extension portions 32, 34 extending from a periphery of the base portion 30. Generally, the extension portions 32, 34 are shaped like curve plate elements. As the connector elements 20, 22 are identical, the same reference numerals will be used to describe the components and parts of each connector element 20, 22. The outer extension portion 32 includes a slot 40 and the inner extension portion 34 includes a pin 42. When the connector elements 20, 22 are initially mated together in an axial direction, the inner extension portion 34 of one connector element 20 fits radially within the outer extension portion 32 of the other connector element 22, and vice-versa. Therefore, the pin 42 of one connector element 20 will be received within the slot 40 of the other connector element 22 and vice-versa. As shown in FIGS. 4 and 5A-5C, each connector element 20, 22 is assembled together with a face seal element 50. Like the connector elements 20, 22, the face seal elements are identically designed. Therefore, the two mating halves of the connector 10 are identical and this provides advantages related, for example, to cost of manufacture and inventory, as well as use of the connector. The face seal element 50 includes a receiving portion 52 that holds an elastomeric, annular seal 54 as well as a barbed, generally cylindrical protrusion 56 having a passage 58 aligning with a central passage 60 in the annular, elastomeric seal 54. The barbed protrusion 56, in this embodiment, is slightly tapered and receives the flexible tubing 12 or 14 with a friction fit. As best shown in FIG. 5A, each face seal element 50 is inserted into a central aperture or passage 70 of the corresponding connector element 20, 22 and a snap fit connection is made between the face seal element 50 and the structure of the connector element 20 or 22 surrounding the central aperture or passage 70. For example, the aperture or passage 70 includes resilient tab members 72 that are biased radially outward as the face seal element 50 is pushed through the aperture or passage 70. When a step or steps 76 on the outer surface of the protrusion 56 of the face seal element 50 pass by the resilient tabs 72, the face seal element 50 is locked into position as shown in FIG. 5A. Thus, the face seal element 50 may not move or translate along the longitudinal axis of the connector 10 and of the tubing 12, 14. However, each face seal element 50 in this embodiment may rotate about the axis for reasons described below.

Figure 5B:
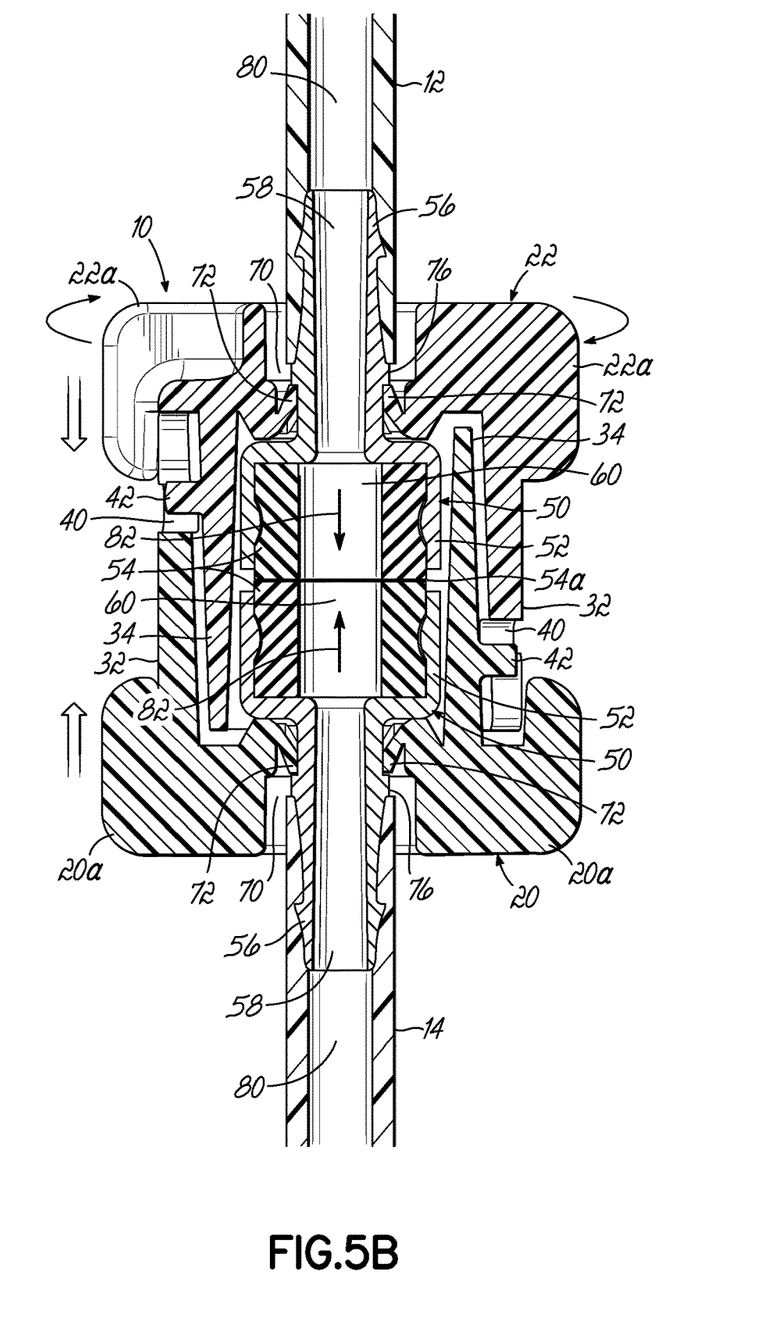
FIG. 5B is a longitudinal axial cross sectional view of the system with the connector elements mated to each other but not yet fully coupled together.
Figure 5C:
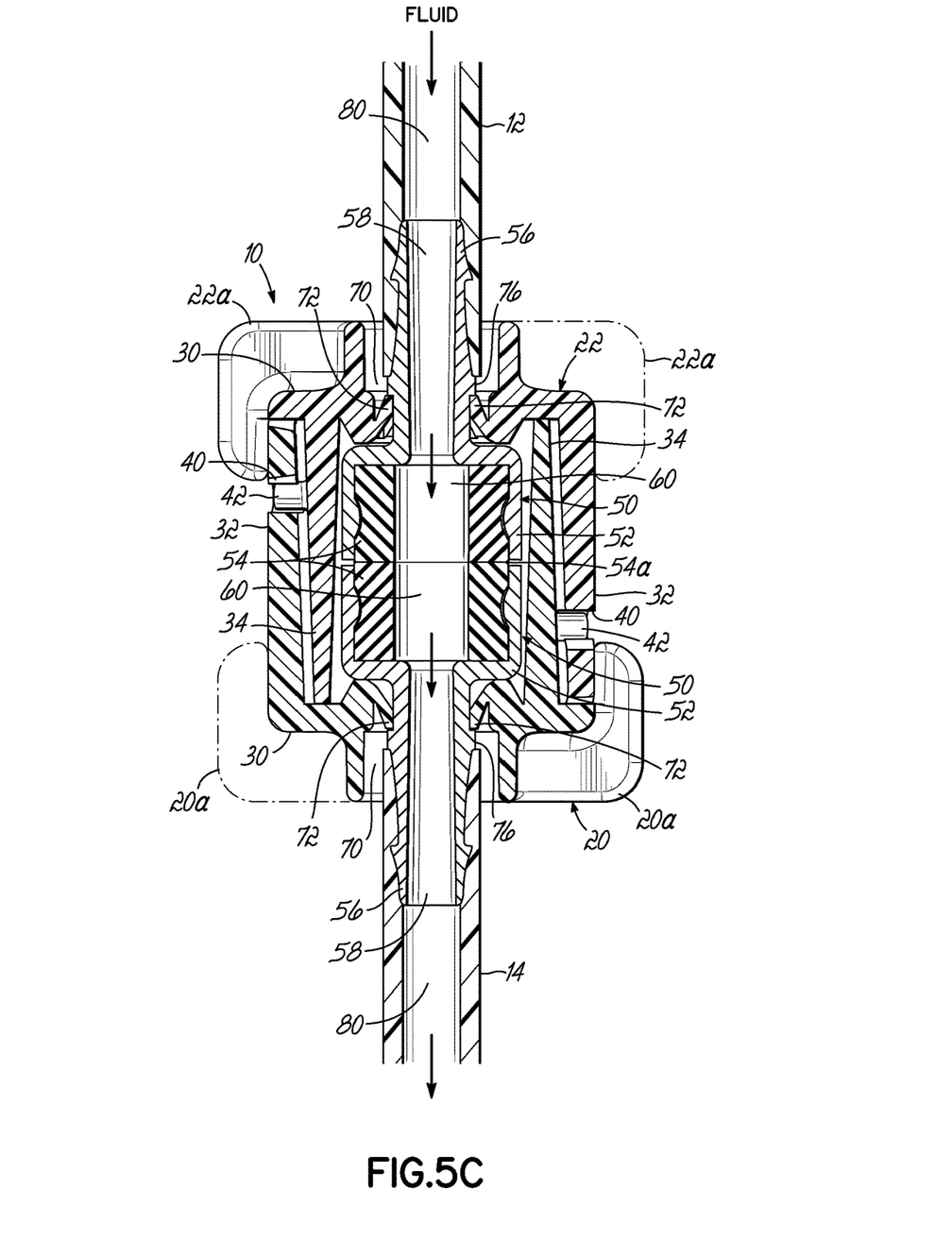
FIG. 5C is a longitudinal axial cross sectional view of the system with the connector elements fully coupled to each other.

FIGS. 5B and 5C illustrate respective positions of the connector elements 20, 22 and their associated face seal elements 50 before full rotation of the connector elements 20, 22 through the 26° turn mentioned above, but after initial contact of the elastomeric seals 54. As shown in FIGS. 5B and 5C, a fluid passageway 80 is formed between the respective lengths of silicone tubing 12, 14, through the respective protrusions 56 of the face seal elements 50, and through the respective passages 60 of the elastomeric seals 54. As at least one of the connector elements 20, 22 is rotated with respect to the other connector element 20, 22 and the pins 42 previously described are traveling within the slots 40 through the 26° turn, the engaging elastomeric seals 54 are compressing against each other. In this regard, their annular faces 54a are in engagement, as shown, and are compressing against each other to form a fluid tight joint between the seals 54. As the connector element(s) 20, 22 is/are rotated, relative rotation is permitted between each face seal element 50 and its associated connector element 20 or 22. This relative rotation is allowed by the snap fit connection previously described and ensures that sliding friction between the engaging, sealing surfaces 54a of the elastomeric seals 54 does not occur. Rather, only an axial compressive engagement occurs as illustrated by the arrows 82 in FIG. 5B. When the respective pins 42 are fully seated within the ends of the slots 40 (FIG. 4), the connector elements 20, 22 are locked together in the position shown in FIG. 5C. It will also be understood from a review of FIG. 4 that the pins 42 will initially travel along a ramped surface 40a of the associated slot 40 and then be forced over a slight detent 40b into the end 40c of the slot 40 after 26° of rotation. This places the connector 10 into a locked, fluid tight condition for facilitating the flow path 80. When it is desired to de-couple the connector 10, one or both of the connector elements 20, 22 are rotated by the user in the opposite direction to that shown and described above. After rotating in the opposite direction 26°, the two connector elements 20, 22 and two lengths of tubing 12, 14 as well as the associated face seal elements 50 are separated as shown in FIG. 5A.

As mentioned above, the connector 10 may be reused for various purposes. In one example, the connector 10 and tubing 12, 14 may be part of a portable pump system. If it is desired to move the portable pump (not shown) to a different location, such as when moving a patient to a different room, the connector 10 may be uncoupled while leaving the tubes 12, 14 coupled to the connector elements 20, 22. The same connector elements 20, 22 may be coupled together again or only one of the connector elements 20 or 22 may be reused and coupled to another identical connector element.

While the present invention has been illustrated by the description of one or more embodiments thereof, and while the embodiments have been described in considerable detail, they are not intended to restrict or in any way limit the scope of the appended claims to such detail. The various features as described herein may be used in the described combinations or in any combination according to the needs of the user. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A fluid connector, comprising:

first and second fluid connector elements including respective first and second base portions, the first and second fluid connector elements each including a pair of extension portions extending from the respective first and second base portions;

first and second face seal elements, the first and second face seal elements respectively carried by the first and second base portions and contained within the pair of extension portions of the associated fluid connector element, the first and second face seal elements respectively comprising a receiving portion holding an annular seal and a protrusion having a passage aligned with a central passage in the annular seal; and a locking coupling configured to couple the first and second fluid connector elements together with the first and second face seal elements in facing and sealing engagement, and then to be rotated relative to one another and locked together to form a fluid tight joint between the first and second face seal elements, thereby forming a fluid flow path through the first and second face seal elements and the first and second fluid connector elements, wherein the first face seal element rotates with respect to the first fluid connector element as the first and second fluid connector elements are rotated relative to one another, and wherein each of the first and second face seal elements is configured to be inserted in a central aperture of the respective fluid connector element, the central aperture including a resilient tab member configured to bias radially outward when the protrusion extends through the central aperture, each of the first and second face seal elements comprising one or more steps on an outer surface of the protrusion adapted to cooperate with the tab member to axially lock the face seal element with respect to the corresponding connector element.

2. The fluid connector of claim 1, wherein the second face seal element rotates with respect to the second fluid connector element as the first and second fluid connector elements are rotated relative to one another.

3. The fluid connector of claim 1, wherein the first and second fluid connector elements are identical.

4. The fluid connector of claim 3, wherein the first and second face seal elements are identical.

5. The fluid connector of claim 1, wherein the locking coupling comprises a pin received on the first fluid connector element and a slot received on the second fluid connector element.

6. A fluid system, comprising:
   first and second fluid connector elements including respective first and second base portions, the first and second fluid connector elements each including a pair of extension portions extending from the respective first and second base portions;
   first and second face seal elements, the first and second face seal elements respectively carried by the first and second base portions and contained within the pair of extension portions of the associated fluid connector element, the first and second face seal elements respectively comprising a receiving portion holding an annular seal and a protrusion having a passage aligned with a central passage in the annular seal;
   first and second tubes respectively coupled to the first and second face seal elements; and
   a locking coupling configured to couple the first and second fluid connector elements together with the first and second face seal elements in facing and sealing engagement, and then to be rotated relative to one another and locked together to form a fluid tight joint between the first and second face seal elements, thereby forming a fluid flow path through the first and second face seal elements, the first and second fluid connector elements and the first and second tubes,
   wherein the first face seal element rotates with respect to the first fluid connector element as the first and second fluid connector elements are rotated relative to one another, and wherein each of the first and second face seal elements is configured to be inserted in a central aperture of the respective fluid connector element, the central aperture including a resilient tab member configured to bias radially outward when the protrusion extends through the central aperture, each of the first and second face seal elements comprising one or more steps on an outer surface of the protrusion adapted to cooperate with the tab member to axially lock the face seal element with respect to the fluid connector element.

7. The fluid system of claim 6, wherein the second face seal element rotates with respect to the second fluid connector element as the first and second fluid connector elements are rotated relative to one another.

8. The fluid system of claim 6, wherein the first and second fluid connector elements are identical.

9. The fluid system of claim 8, wherein the first and second face seal elements are identical.

10. The fluid system of claim 6, wherein the locking coupling comprises a pin received on the first fluid connector element and a slot received on the second fluid connector element.

11. A method of forming a fluid tight connection, the method comprising:
   inserting first and second face seal elements in a central aperture of a respective first and second fluid connector element, the central aperture including a resilient tab member configured to bias radially outward when a protrusion extends through the central aperture, each of the first and second face seal elements comprising one or more steps on an outer surface of the protrusion adapted to cooperate with the tab member to axially lock the face seal element with respect to the fluid connector element;
   mating the first and second fluid connector elements such that the respective first and second face seal elements carried within the first and second fluid connector elements are in opposed contact, the first and second face seal elements respectively comprising a receiving portion holding an annular seal and the protrusion having a passage aligned with a central passage in the annular seal;
   rotating at least one of the first or second fluid connector elements with respect to one another while the first face seal element rotates with respect to the first fluid connector element to axially force the first and second face seal elements into sealing engagement; and
   locking the first and second fluid connector elements such that the first and second face seal elements form a fluid tight joint and a fluid flow path is formed through the first and second face seal elements and the first and second fluid connector elements.

12. The method of claim 11, wherein locking the first and second fluid connector elements comprises rotating the first and second fluid connector elements such that a pin of the first fluid connector element is lockingly received within a pin defined within the second fluid connector element.

* * * * *